(12) United States Patent
Cloete et al.

(10) Patent No.: US 10,633,551 B2
(45) Date of Patent: Apr. 28, 2020

(54) ANTIMICROBIAL SOLUTION

(71) Applicant: STELLENBOSCH UNIVERSITY, Stellenbosch (ZA)

(72) Inventors: William Cloete, Stellenbosch (ZA); Lubertus Klumperman, Leiderdorp (NL)

(73) Assignee: Stellenbosch University, Stellenbosch (ZA)

( * ) Notice: Subject to any disclaimer, the term of this patent is extended or adjusted under 35 U.S.C. 154(b) by 55 days.

(21) Appl. No.: 15/900,338

(22) Filed: Feb. 20, 2018

(65) Prior Publication Data
US 2018/0237653 A1   Aug. 23, 2018

(30) Foreign Application Priority Data
Feb. 21, 2017  (GB) .................................. 1702804.4

(51) Int. Cl.
| | | |
|---|---|---|
| C09D 123/36 | (2006.01) | |
| C09D 5/14 | (2006.01) | |
| A61L 15/44 | (2006.01) | |
| C08F 8/32 | (2006.01) | |
| C08F 212/08 | (2006.01) | |
| C08F 8/14 | (2006.01) | |
| C09D 7/65 | (2018.01) | |

(Continued)

(52) U.S. Cl.
CPC ............ *C09D 123/36* (2013.01); *A61L 15/44* (2013.01); *A61L 15/46* (2013.01); *A61L 31/16* (2013.01); *C08F 8/14* (2013.01); *C08F 8/32* (2013.01); *C08F 8/44* (2013.01); *C08F 212/08* (2013.01); *C09D 5/14* (2013.01); *C09D 7/65* (2018.01); *C09D 125/08* (2013.01); *A61L 2300/208* (2013.01); *A61L 2300/404* (2013.01); *C08F 2810/50* (2013.01)

(58) Field of Classification Search
None
See application file for complete search history.

(56) References Cited

FOREIGN PATENT DOCUMENTS

| | | |
|---|---|---|
| CN | 101824115 A | 9/2010 |
| CN | 102302904 A | 1/2012 |
| WO | 2011/095867 A1 | 8/2011 |

*Primary Examiner* — Robert A Wax
*Assistant Examiner* — Danah Al-Awadi
(74) *Attorney, Agent, or Firm* — Eric J. Sosenko; Jonathan P. O'Brien; Honigman LLP

(57) ABSTRACT

A solution including an antimicrobial polymer in a polar solvent and a method of producing the solution. The polymer has the structure of Formula (I). The antimicrobial solution may be coated onto a substrate and cured to provide an antimicrobial substrate in which the polymer is covalently bonded to the substrate so that it cannot leach from the substrate.

Formula (I)

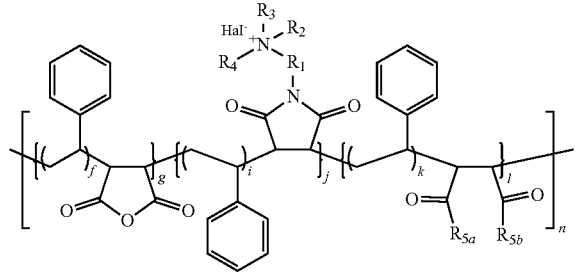

15 Claims, 2 Drawing Sheets
(1 of 2 Drawing Sheet(s) Filed in Color)

(51) Int. Cl.
*C09D 125/08* (2006.01)
*C08F 8/44* (2006.01)
*A61L 15/46* (2006.01)
*A61L 31/16* (2006.01)

ANTIMICROBIAL SOLUTION

FIELD OF THE INVENTION

This invention relates to an antimicrobial solution to be applied as a coating to a suitable substrate. In particular it relates to a solution for use in providing a polymeric antimicrobial coating including quaternary ammonium moieties.

BACKGROUND TO THE INVENTION

Antimicrobial coatings are applied to substrates such as wound dressings, personal hygiene or sanitary products, clothing, packaging, furniture, construction materials, textiles and the like to make them sterile and prevent bacterial growth. Antimicrobial coatings find particular use in wound dressings as the exudate from the wound contained in an absorptive wound dressing typically encourages the growth of bacteria, resulting in infections that compromise wound healing.

Most antimicrobial coatings include antimicrobial agents that are not permanently bonded to the substrate and eventually leach from the coating or are released from it. Such coatings lose their efficacy over time and the microbes may develop resistance against the particular active agents. Antimicrobial wound dressings, for example, normally include low molar mass biocides or nanosilver that leach from the coating and affects bacterial growth in its immediate environment. Due to the mode of action and activity of biocides and nanosilver, antimicrobial efficacy is lost over time and cannot be regenerated. Moreover, the antimicrobial agents may in some instances have a toxic or harmful effect if concentrations are increased in an attempt to prolong efficacy.

There is thus a need for an antimicrobial coating that may be permanently bonded to a substrate and which has the required antimicrobial activity to protect the substrate and surrounding environment from microbial infection, whilst retaining its antimicrobial activity for extended periods of time.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with the invention, there is provided a solution including an antimicrobial polymer having the structure of Formula (I):

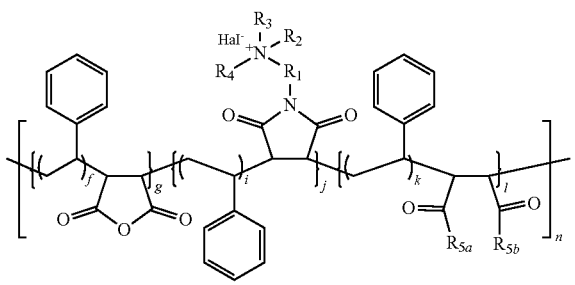

Formula (I)

wherein $R_1$ is a $C_2$-$C_7$ alkyl;
$R_2$ is a $C_8$-$C_{15}$ alkyl;
$R_{5a}$ is $O^-$ or OH and $R_{5b}$ is $OR_6$, or $R_{5b}$ is $O^-$ or OH and $R_{5a}$ is $OR_6$;
$R_3$, $R_4$ and $R_6$ are each independently a $C_1$-$C_4$ alkyl;
Hal$^-$ is a halide anion selected from the group consisting of bromide (Br$^-$), chloride (Cl$^-$) and iodide (I$^-$);
f, i, j, k and l are each independently an integer from 1 to 100;
g is an integer from 0 to 100;
the ratio of j:l is from about 1:1 to 19:1; and
$0.1 < j/(g+j+l) < 1.0$; in a polar solvent.

A further feature of the invention provides for the ratio of j:l to be from about 4:1 to 9:1.

A still further feature provides for f, i and k to each independently be an integer from 1 to 4.

Yet further features of the invention provide for $R_1$ to be a $C_2$-$C_3$ alkyl; for $R_2$ to be a $C_9$-$C_{12}$ alkyl; for $R_3$ and $R_4$ to be methyl groups; and for Hal$^-$ to be bromide (Br$^-$).

Even further features of the invention provide for the polar solvent to be a high boiling point solvent; for the polar high boiling point solvent to be dimethyl sulfoxide, dimethyl acetamide or dimethylformamide; and for the concentration of the antimicrobial polymer in the solution to be about 30 to 35 wt %.

Still further features of the invention provide for the solution to include a low boiling point solvent which is miscible with the high boiling point solvent and in which the polymer is soluble, for the low boiling point solvent to be a linear or branched alcohol, preferably selected from the group consisting of methanol, ethanol, propanol and isopropanol; and for the polymer to be present in the solution at a sufficient concentration to inhibit growth of gram positive and/or gram negative bacteria, preferably at a concentration of about 0.1 to 20 wt %.

In accordance with a second aspect of the invention, there is provided a method of producing a solution including an antimicrobial polymer having the structure of Formula (I):

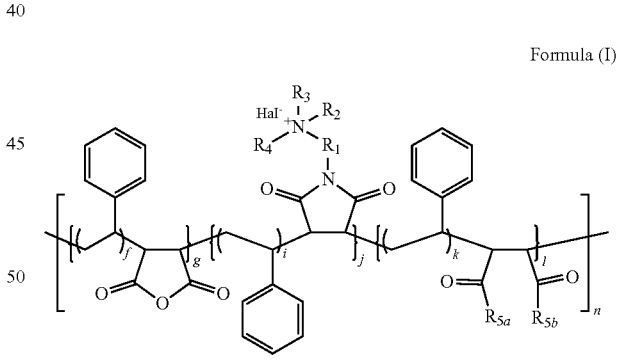

Formula (I)

wherein $R_1$ is a $C_2$-$C_7$ alkyl;
$R_2$ is a $C_8$-$C_{15}$ alkyl;
$R_{5a}$ is $O^-$ or OH and $R_{5b}$ is $OR_6$, or $R_{5b}$ is $O^-$ or OH and $R_{5a}$ is $OR_6$;
$R_3$, $R_4$ and $R_6$ are each independently a $C_1$-$C_4$ alkyl;
Hal$^-$ is a halide anion selected from the group consisting of bromide (Br$^-$), chloride (Cl$^-$) and iodide (I$^-$);
f, i, j, k and l are each independently an integer from 1 to 100;
g is an integer from 0 to 100;
the ratio of j:l is from about 1:1 to 19:1; and
$0.1 < j/(g+j+l) < 1.0$; the method being carried out in a polar solvent and comprising the steps of:

reacting poly(styrene-co-maleic anhydride) copolymer with N,N-dimethyl-3-amino($C_2$-$C_7$)alkyl-1-amine to form poly(styrene-co-N—(N',N'-dimethylamino($C_2$-$C_7$)alkyl)-maleimide); and reacting the poly(styrene-co-N—(N',N'-dimethyl-3-amino($C_2$-$C_7$)alkyl)-maleimide) with a $C_8$-$C_{15}$ alkyl bromide, chloride or iodide to produce the polymer of Formula (I).

Further features of this aspect of the invention provide for the reactions to be carried out consecutively in the same solvent; for the solvent to be a high boiling point solvent such as DMSO, DMAC or DMF; for the solution containing the polymer of Formula (I) to be diluted with a low boiling point solvent; and for the low boiling point solvent to be a linear or branched alcohol, preferably selected from the group consisting of methanol, ethanol, propanol and isopropanol.

Yet further features of this aspect provide for a selected amount of N,N-dimethyl-3-amino($C_2$-$C_7$)alkyl-1-amine to be reacted with the poly(styrene-co-maleic anhydride) copolymer that is less than the molar equivalent of maleic anhydride residues in the poly(styrene-co-maleic anhydride); and for the selected amount to be 80-90 mol % of the total maleic anhydride in the poly(styrene-co-maleic anhydride) to produce a polymer of Formula (I) in which about 80-90% of the maleic anhydride residues are converted into N—(N',N'-dimethyl-3-amino($C_2$-$C_7$)alkyl)-maleimide residues and 10%-20% of the maleic anhydride residues remain unmodified.

Still further features of this aspect provide for the poly(styrene-co-maleic anhydride) copolymer to be reacted with N,N-dimethyl-3-aminopropyl-1-amine to form poly(styrene-co-N—(N',N'-dimethylaminopropyl)-maleimide); and for the poly(styrene-co-N—(N',N'-dimethyl-3-aminopropyl)-maleimide) to be reacted with 1-bromodecane.

In accordance with a third aspect of the invention, there is provided a method of producing an antimicrobial substrate comprising the steps of:

at least partially coating a substrate or a surface thereof with the solution including the antimicrobial polymer of Formula (I) described above; and curing the coating to crosslink the polymer of Formula (I) to the substrate.

A further feature of this aspect provides for the curing step to involve heating the substrate under vacuum, preferably heating the substrate to about 100° C. to 110° C. under vacuum for about 1 hour.

The invention also provides an antimicrobial substrate, which includes a polymer of Formula (I)

$R_{5a}$ is $O^-$ or OH and $R_{5b}$ is $OR_6$, or $R_{5b}$ is $O^-$ or OH and $R_{5a}$ is $OR_6$;

$R_3$, $R_4$ and $R_6$ are each independently a $C_1$-$C_4$ alkyl;

Hal$^-$ is a halide anion selected from the group consisting of bromide (Br$^-$), chloride (Cl$^-$) and iodide (I$^-$);

f, i, j, k and l are each independently an integer from 1 to 100;

g is an integer from 0 to 100;

the ratio of j:l is from about 1:1 to 19:1; and $0.1 < j/(g+j+l) < 1.0$; crosslinked to the substrate.

Further features provide for the substrate to be a wound dressing, gauze, burn dressing, sponge, a medical or sanitary wipe, surgical gown, surgical glove, surgical scrubs, upholstery, floor mat, sheet, cover, liner, curtain or insole, most preferably a wound dressing; and for the wound dressing to be made of an absorptive textile.

An embodiment of the invention will now be described, by way of example only, with reference to the accompanying figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

In the Figures.

DETAILED DESCRIPTION OF THE INVENTION

Figure 1:
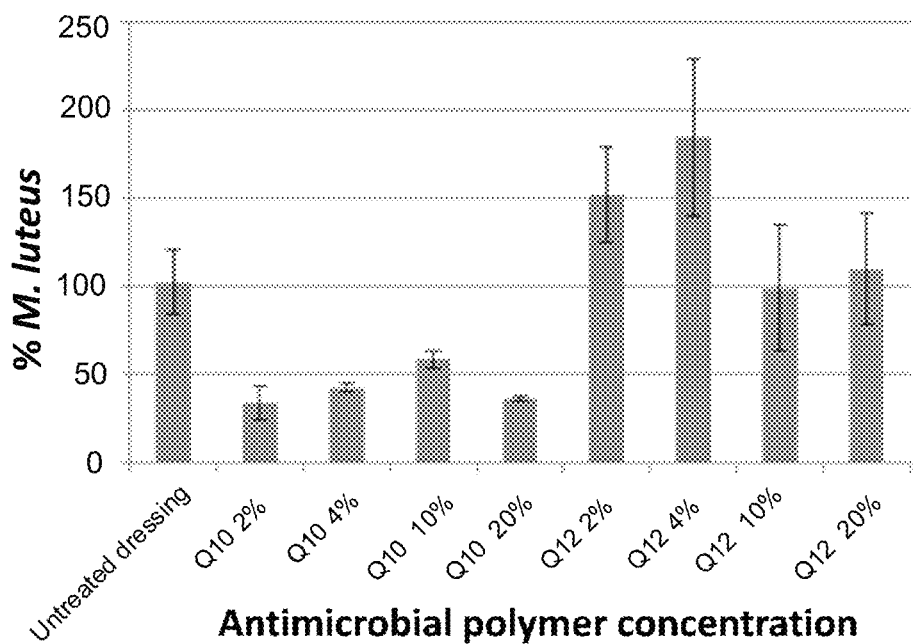
FIG. 1 is a bar graph that plots the percentage cell viability of *Micrococcus luteus* bacteria on dressing samples treated with different concentrations of Polymer II (Q10) and Polymer III (Q12) antimicrobial polymer coating solutions.

A solution comprising an antimicrobial polymer having the structure of Formula (I):

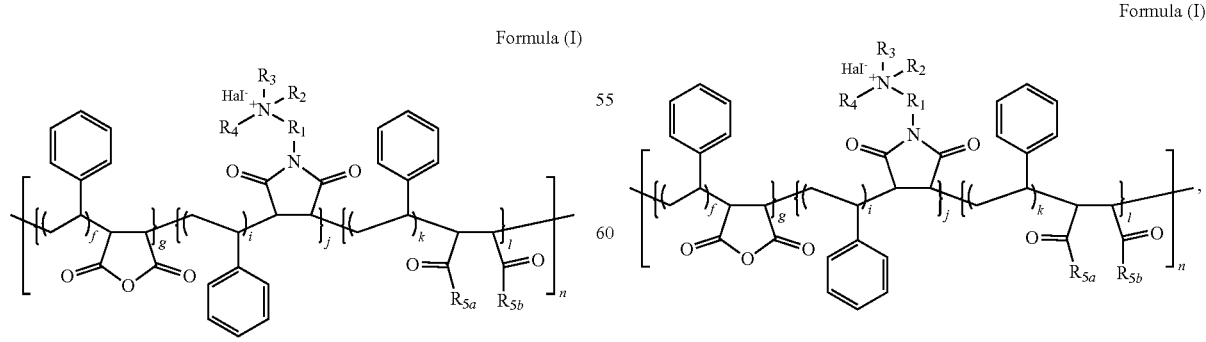

Formula (I)

wherein $R_1$ is a $C_2$-$C_7$ alkyl;
$R_2$ is a $C_8$-$C_{15}$ alkyl;

wherein $R_1$ is a $C_2$-$C_7$ alkyl; $R_2$ is a $C_8$-$C_{15}$ alkyl; $R_{5a}$ is $O^-$ or OH and $R_{5b}$ is $OR_6$, or $R_{5b}$ is $O^-$ or OH and $R_{5a}$ is $OR_6$; $R_3$, $R_4$ and $R_6$ are each independently a $C_1$-$C_4$ alkyl; Hal$^-$ is a halide anion selected from the group consisting of bromide (Br⁻), chloride (Cl⁻) and iodide (I⁻); f, i, j, k and l are each independently an integer selected from 1 to 100; g is an integer from 0 to 100; the ratio of j:l is from about 1:1 to 19:1; and $0.1<j/(g+j+l)<1.0$; in a polar solvent, is provided.

The polymer of Formula (I) includes quaternary ammonium salt moieties on the modified maleic anhydride residues that provide the polymer with antimicrobial activity. The quaternary ammonium salt moieties include a $C_8$-$C_{15}$ alkyl group ($R_2$), which in some embodiments is a $C_{10}$ alkyl group. The maleic anhydride residues (MAnh) in a poly (styrene-co-maleic anhydride) copolymer (SMA) can be modified to include antimicrobial quaternary ammonium salt groups by:
  (i) nucleophilic addition to the MAnh residues of N,N-dimethyl-3-amino($C_2$-$C_7$)alkyl-1-amine (DMAAA) in which the alkyl group ($R_1$) consists of 2 to 7 carbon atoms, preferably 2 to 3 carbon atoms, and more preferably, 3 carbon atoms where the DMAAA is N,N-dimethyl-3-aminopropyl-1-amine (DMAPA) to form a tertiary amine group; and
  (ii) subsequent alkylation of the tertiary amine group with an alkyl halide.

The ratio of styrene monomers to MAnh monomers in the SMA and in the polymer of Formula (I) can be from about 1:1 (that is about 50% each) to about 4:1 (that is about 80% styrene to 20% MAnh). In other words, f, i and k can each independently be an integer from 1 to 4. The ratio of j:l in Formula (I) may be from about 4:1 to about 9:1, wherein only 80-90 mol % of the MAnh residues are functionalised with the antimicrobial quaternary ammonium groups. This can be achieved by reacting only 80 to 90 mol % of MAnh residues in the bulk SMA copolymer with DMAAA and subsequently with alkyl halide such that 10-20% of the MAnh residues remain unsubstituted. The 10-20% MAnh residues may be modified in solution or functionalised with a second type of molecule to provide the polymer with a second functionality in addition to its antimicrobial properties. As is evident from Formula (I) and the definition of f, i and k, there is at least one styrene monomer between every two MAnh monomers.

The ratio of j to g+l is the degree of modification of the polymer. The larger the fraction of modified MAnh sub-units (j), the larger the antimicrobial effect. However, for adhesion to a substrate it is necessary for the polymer to include at least some unmodified MAnh (g) or ester (l) sub-units. The proportion of modified sub-units (j) is between 10% and 100%, i.e. $0.1<j/(g+j+l)<1.0$. In some embodiments this can be between 50% and 90%, i.e. $0.5<j/(g+j+l)<0.9$ or between 75% and 90%, i.e. $0.75<j/(g+j+l)<0.9$.

The SMA copolymer is a statistical copolymer with a weight average molar mass of from about 2,000-600,000 g·mol⁻¹, equivalent to approximately 20-6000 monomeric units of styrene and MAnh combined. The antimicrobial polymer of Formula (I) can also contain a corresponding 20-6000 monomeric units of styrene and MAnh. The integer n in Formula (I) has the usual meaning of indicating the repetition of monomer residues to the indicated total number of 20-6000.

The polymer of Formula (I) may be synthesised in a polar, high boiling point solvent such as dimethyl sulfoxide, dimethyl acetamide or dimethylformamide. In this specification, the phrase "high boiling point solvent" shall be interpreted to mean any solvent having a boiling point of 100° C. or more at 101.325 kPa. The phrase "low boiling point solvent" shall be interpreted to mean a solvent having a boiling point of less than 100° C. at 101.325 kPa.

The quantities of the reactants are selected to initially form a concentrated solution of the polymer, preferably having a concentration of about 30 to 35 wt % in the polar, high boiling point solvent. This concentrated solution is also referred to herein as an "antimicrobial resin". The resin may be provided for on-site dilution and coating. A polymer concentration of 0.1 to 20 wt % may be used during the coating and curing process to produce a substrate with the polymer crosslinked thereto and having the desired antimicrobial activity. The resin may be diluted with an appropriate low boiling point solvent which is miscible with the high boiling point solvent and in which the polymer of Formula (I) is soluble, such as a branched or linear alcohol selected from the group consisting of methanol, ethanol, propanol or iso-propanol. In the event that the resin is a DMSO solution of the polymer, the solution may be diluted with methanol. Accordingly, a 30 to 35 wt % DMSO solution may, for example, be diluted with methanol to a concentration in which the polymer coating will be effective in inhibiting bacterial growth of gram positive and gram negative bacteria, i.e. to about 0.1 to 20 wt %.

Some or all of the 10-20 mol % MAnh residues that remain unmodified in the polymer chain convert to hemi-esters, also referred to herein as a vicinal monoesterified dicarboxylic acid group, by reaction with the methanol in solution. This reaction will also take place with any other polar branched or unbranched alcohol, such as ethanol, propanol, isopropanol, butanol or isobutanol, which is miscible with the DMSO, DMAC or DMF to form the corresponding hemi-ester in solution. The hemi-esters are represented in sub-unit I of Formula (I). As the alcohol can equally react with either carbonyl group on the MAnh, the hemi-ester can be formed with the ester at either one of $R_{5a}$ and $R_{5b}$ and the carboxylic acid at the other. These ring-opened MAnh derivatives are able to covalently link to appropriate functional groups on a substrate such as a textile.

The polymer of Formula (I) may be produced by a one-pot or batch modification process, which is easy to scale up. The method comprises a first step of reacting 80-90 mol % of the available MAnh residues in the bulk polymer with N,N-dimethyl-3-amino($C_2$-$C_7$)alkyl-1-amine (DMAAA) to form poly(styrene-co-N—(N',N'-dimethyl-3-amino($C_2$-$C_7$) alkyl)-maleimide) in which 80-90% of the MAnh residues are modified with DMAAA. With the end-function or application of the polymer in an antimicrobial coating solution to be applied to a substrate in mind, the imidization is carried out with a sub-molar amount of the amine, DMAAA. The degree of imidization determines the remaining amount of maleic anhydride monomers in the polymer which are available to crosslink to the substrate so as to covalently bind the antimicrobial polymer to the substrate. The nucleophilic addition of DMAAA to SMA is carried out in DMF, DMAC or DMSO at room temperature or at about 40 to 60° C. The reaction occurs via an open ring acid-amide intermediate which precipitates. The reaction is gradually heated to about 100-110° C. to result in ring closure and the formation of a maleimide residue upon loss of $H_2O$. Next, the reaction is cooled to about 75-85° C. and a corresponding molar equivalent (80-90 mol % MAnh in the bulk polymer) of a selected alkyl halide, i.e. a $C_8$-$C_{15}$ alkyl bromide, $C_8$-$C_5$ alkyl chloride or $C_8$-$C_{15}$ alkyl iodide, is added to the reaction medium containing the previously formed poly(styrene-co-N—(N',N'-dimethyl-3-amino($C_2$-$C_7$)alkyl)-maleimide polymer to produce the polymer of Formula (I) via a nucleophilic substitution reaction of the alkyl halide with the tertiary amine group of DMAAA to form a quaternary ammonium salt. The reaction takes about 6 hours at 75-85° C. to proceed to completion.

The synthesis of the polymer of Formula (I) may be via a one-pot or batch modification synthesis with both reactions carried out consecutively in the same high boiling point solvent such as DMSO, DMAC or DMF. The method does not require the polymer to be isolated between consecutive steps, which simplifies the synthesis and makes it less costly. The antimicrobial coating solution may be synthesized on large scale in commercially available reaction vessels (60-250 L).

A preferred quaternary ammonium salt is formed on the SMA polymer backbone by reacting the SMA copolymer with N,N-dimethyl-3-aminopropyl-1-amine (DMAPA) and 1-bromodecane, i.e. a polymer of Formula (I) in which $R_1$=a $C_3$ alkyl chain, $R_2$=a $C_{10}$ alkyl chain and $Hal^-$ is a bromide.

In one embodiment, 90 mol % of the MAnh units in the bulk polymer is reacted with the DMAAA such that about 90 mol % of the MAnh residues of the SMA copolymer are modified with DMAAA, and subsequently with an alkyl halide to produce the quaternary ammonium salt moieties. By ensuring that DMAAA is the limiting reagent, there should be no residual, unreacted DMAAA or alkyl halide in the produced antimicrobial coating solution provided that both reactions proceed to completion. Residual reactants are undesirable as they may be toxic and leach from the coating once applied to a substrate. Furthermore, if remaining 10% of the MAnh residues that are not functionalized with DMAAA and the alkyl halide are free to be functionalized with any other molecule.

The quantities of the reactants and solvents are selected to initially produce a concentrated solution or resin of the polymer of Formula (I). This resin can then be diluted prior to use with a low boiling point solvent, preferably methanol to any required weight percentage of polymer in the antimicrobial coating solution, preferably to 0.1-20 wt %.

An antimicrobial substrate may be produced by at least partially coating the solution containing the antimicrobial polymer described above onto a substrate or a surface thereof, curing the coating to crosslink the polymer to the substrate, and removing the solvents. The resin may first be diluted to a 0.1 to 20 wt % concentration with methanol before application to the substrate. Dilution of the resin with methanol results in the conversion of the available MAnh residues to a vicinal monoesterified dicarboxylic acid group or hemi-ester which is able to covalently bond with a substrate. The curing step may be carried out at about 100° C. to 110° C. under vacuum for about 1 hour. The curing step necessarily involves drying the coating by evaporatively removing the low-boiling solvent and most of the high boiling point solvent originally forming part of the antimicrobial coating solution. The curing step may optionally be followed by a washing step to remove any polymer or reactants that are physically adsorbed to the substrate and not covalently bonded to it, followed by a further drying step to remove the solvents or reagents used during the washing step. Any solvent that is capable of removing the remaining physically adsorbed but unbonded polymer and any further remaining reactants is suitable for the washing step. It is preferred that the washing step is carried out with the same low boiling point solvent that was used to dilute the polymer resin prior to coating, such as methanol.

The substrate should ideally have available hydroxyl or carboxylic acid groups to enable the polymer of Formula (I) to be covalently bonded to the substrate. The covalent bonds are strong enough to substantially avoid leaching of the antimicrobial polymer coating from the substrate. Any type of substrate made of natural or synthetic material may be coated with the antimicrobial polymer of Formula (I), provided it has the requisite functional groups for covalent bonds to be formed on its surface.

The antimicrobial coating solution may be used to provide substrates such as wound dressings, gauzes, burn dressings, sponges, medical or sanitary wipes, surgical gowns, surgical gloves, surgical scrubs, upholstery, floor mats, sheets, covers, liners, curtains or insoles, personal hygiene or sanitary products, clothing, packaging, furniture, construction materials, textiles and the like with a coating having antimicrobial properties.

In particular the antimicrobial coating solution may be applied to a textile made of polyester or cellulosic fibers, such as those used in biocompatible and absorptive wound dressings. The coating step may include dipping the textile in the antimicrobial coating solution prior to curing it to covalently bond the polymer coating to the dressing. A coating and curing process may be devised for high throughput coating and curing of a textile, for example, in an assembly line. The textile may be dipped into a bath of the coating, passed through squeeze rollers to remove excess antimicrobial coating solution and control the coating thickness and then carried through a series of ovens (either horizontally or vertically) for drying and curing. During the curing step, the solvents from the coating solution are substantially removed so that they do not form part of the wound dressing. If required, the assembly line may also include nozzles that spray a selected washing fluid onto the textile to remove any polymer that is not covalently bonded to the textile as well as any unwanted reagents. In this manner an antimicrobial textile may be produced for use in wound dressings. The antimicrobial polymer of Formula (I) is crosslinked to the dressing and unable to leach from dressing into a wound bed.

Wound dressings are commonly used as part of the standard of care for wound bed preparation. They are usually extremely absorptive and effective at drawing exudate away from the wound surface and removing toxic components such as slough, wound debris and bacteria that compromise wound healing.

To prepare an antimicrobial wound dressing, the whole or part of the dressing may be dipped into the antimicrobial polymer solution in which the polymer of Formula (I) is present at a concentration of about 0.1-20 wt %. The wound dressing is then squeezed or may be drip dried to remove excess antimicrobial coating solution. The wound dressing is then cured, allowing the polymer to crosslink to the polymeric fibers, typically polyester and/or cellulose, of the dressing. The solvent is then removed by heating the dressing under vacuum. It is suspected that the crosslinking of the polymer to the wound dressing fibers proceeds via an intermolecular transesterification reaction. The low boiling point solvent (typically methanol, ethanol, propanol, isopropanol, butanol or isobutanol) which evaporates during the curing step may be recovered and recycled. Next, the wound dressing is soaked and washed with the low boiling point solvent to get rid of any physically adsorbed polymer.

DMSO may be selected as the high boiling point solvent in which the polymer is initially synthesized and dissolved to form the resin, as any possible residual DMSO on the wound dressing should not have a toxic effect. A polymer concentration of between 0.1-1 wt % may be selected to provide the wound dressing with antimicrobial properties whilst not substantially affecting the absorbance of the dressing. It was found that a coating solution with 2 wt % of the polymer of Formula (I) reduced the absorbance of a dressing by about 50%, whereas use of 0.1 wt % solution resulted in substantially no reduction in the absorbance of the dressing. Moreover, partial crosslinking may facilitate the retention of the absorbance of the wound dressing.

EXAMPLES

Synthesis of an Exemplary Antimicrobial Coating Solution Via Two Different Methods The antimicrobial polymer of the Formula (I) can be synthesized by obtaining a commercially available SMA copolymer and modifying it to include the antimicrobial quaternary ammonium moieties or by first synthesising the SMA copolymer.

1. Synthesis of Poly(styrene-co-maleic anhydride) (SMA)

flask equipped with a condenser and dissolved in methyl ethyl ketone (MEK) or any low boiling point polar solvent that is both a good solvent for the monomers as well as the polymer, i.e. ethyl acetate. The amount of the initiator AIBN that was added is based on the total amount of monomers in the reaction. The AIBN was added in 0.1 mol % of the total monomer to obtain a high molar mass polymer. The reaction mixture was degassed by purging with argon for at least 30 minutes before it was heated to 60° C. The reaction was left to react overnight (ca. 15-20 hours) in order to achieve the highest conversion of the monomer. A yield of 98-99% monomer conversion was obtained. The SMA polymer had a molecular weight ($M_w$) of about 400-450 kDA and a ratio of about 1:1 styrene residues to maleic anhydride residues. The results of a batch to batch consistency evaluation of the polymers produced in this step is shown in Table 2 below.

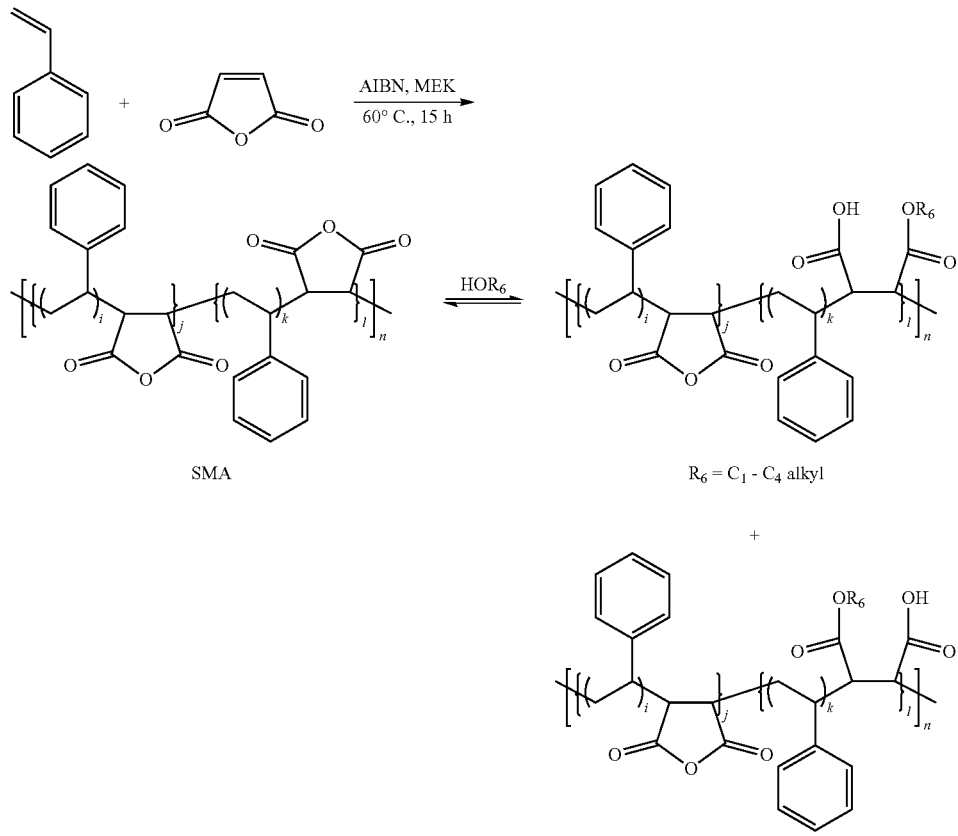

TABLE 1

Quantities of reactants, initiator and solvent used in the reaction.

| Compound | Mass (g) |
|---|---|
| Styrene (Sty) | 15.1 |
| Maleic Anhydride (MAnh) | 14.1 |
| AIBN | 0.1017 |
| MEK | 240 mL |

For the preparation of the base polymer for modification (see Scheme 1) styrene (Sty) and maleic anhydride (MAnh) were polymerised in an approximate 1:1 molar ratio under inert conditions. The monomers were placed in a three neck

TABLE 2

Batch to batch evaluation

| Sample Code | Molar Mass ($M_w$) | Dispersity (Đ) |
|---|---|---|
| Sample 1 | 434 kDa | 1.82 |
| Sample 2 | 402 kDa | 1.77 |
| Sample 3 | 451 kDa | 1.99 |
| Sample 4 | 402 kDa | 2.52 |

Generally the reaction of a 1:1 molar ratio of styrene to maleic anhydride produces a strongly alternating copolymer.

The reaction mixture was cooled down to room temperature and a small amount of high boiling point solvent, DMSO was added). The reaction mixture was transferred into a round bottom flask and placed on a rotary evaporator in order to get rid of the low boiling point solvent. After most of the MEK evaporated, 120 mL of DMSO was added. The flask was then placed back on the rotary evaporator to remove any remaining MEK. After all of the low boiling point solvent was evaporated, a highly concentrated SMA solution in DMSO was obtained.

2. Modification of SMA Copolymer to Produce poly(styrene-co-N—(N',N'-dimethyl-3-aminopropyl)-maleimide (m-SMA)

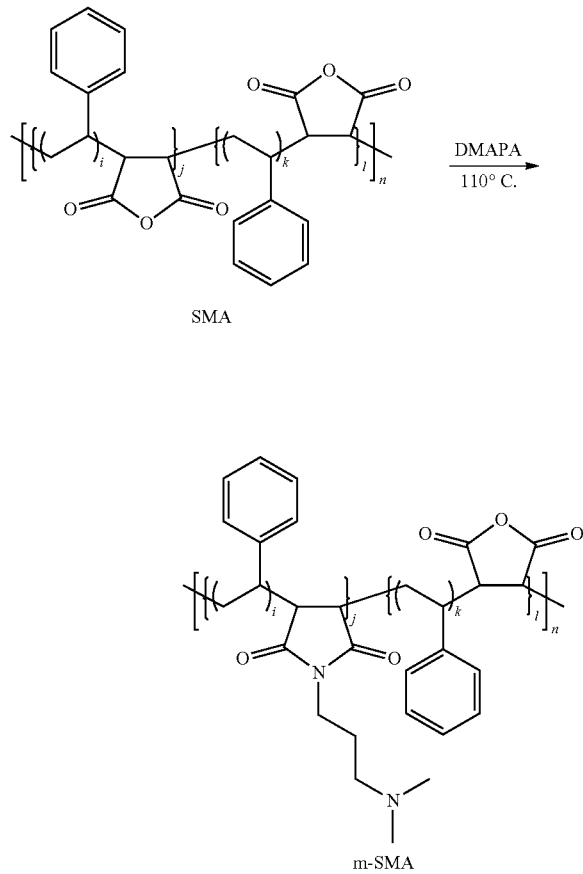

SMA m-SMA 13.1 g of DMAPA (N,N-dimethyl-3-aminopropyl-1-amine), equivalent to 90 wt % of the theoretically available MAnh residues in the polymer, was added to a concentrated DMSO solution of the SMA polymer produced in step 1 above at room temperature under magnetic stirring. Dropwise addition of DMAPA leads to a white or light yellow polymeric precipitate as the ring opening of MAnh proceeds due to nucleophilic addition of DMAPA. The reaction was left for 1-2 hours and subsequently heated to 110° C. The polymer dissolved in DMSO as the ring closure occurs to form modified SMA copolymer (m-SMA) in scheme 2.

3. Modification of m-SMA to Produce an Antimicrobial Polymer, Polymer I, in the Form of a Highly Concentrated Resin

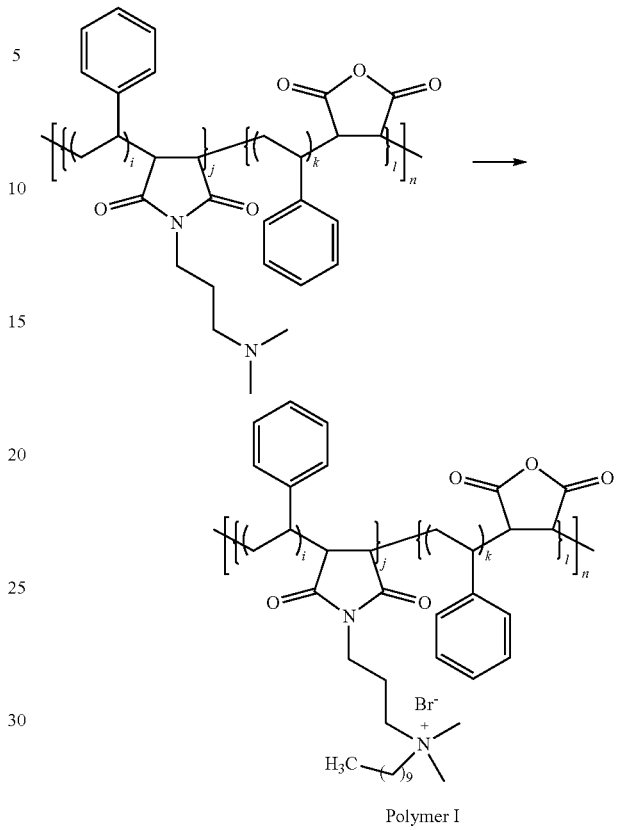

Polymer I

The reaction containing m-SMA produced in step 2 above was cooled down to 80° C. before adding 28.3 g of 1-bromodecane (corresponding to approximately 90 mol % of the maleic anhydride residues of SMA) dropwise to the reaction medium without isolating the polymer from the solution. The alkylation of m-SMA to form Polymer I, as shown in scheme 3, was left to proceed under magnetic stirring for more than 6 hours.

Two antimicrobial polymers, Polymer II (where $R_2$=$C_{10}$ alkyl) and Polymer III (where $R_2$=$C_{12}$ alkyl), having similar structures to Polymer I were synthesised using an alternative method. In this method, commercially available 28% SMA polymer having a molar ratio of styrene to maleic anhydride of 72:28 (supplied by Polyscope™) was used. The polymer was dissolved in a high boiling point solvent in as high a concentration as possible, typically a wt:wt ratio of 1:3 (SMA:DMSO). Steps 2 and 3 described above were then followed using the quantities of reagents and solvent listed in Table 3 below to yield concentrated solutions of Polymer II and Polymer III in DMSO.

TABLE 3

Quantities of reagents and solvent used

| Compound | Mass (g) |
| --- | --- |
| SMA | 10 |
| DMSO | 36 |
| DMAPA | 2.62 |
| For Polymer II: 1-Bromodecane | 5.12 |
| For Polymer III: 1-Bromododecane | 5.77 |

Preparation of the Antimicrobial Coating Solution

Concentrated solutions or resins of Polymer II and Polymer III were diluted with an alcohol, such as methanol, to obtain a series of antimicrobial coating solutions with concentrations ranging between 0.1-20%. The antimicrobial coating solutions included the Polymer II or Polymer III, the alcohol and trace amounts of DMSO. In solution with the alcohol, Polymer II and Polymer III at least partially convert to a vicinal monoesterified dicarboxylic acid group, as shown in Scheme 4 below.

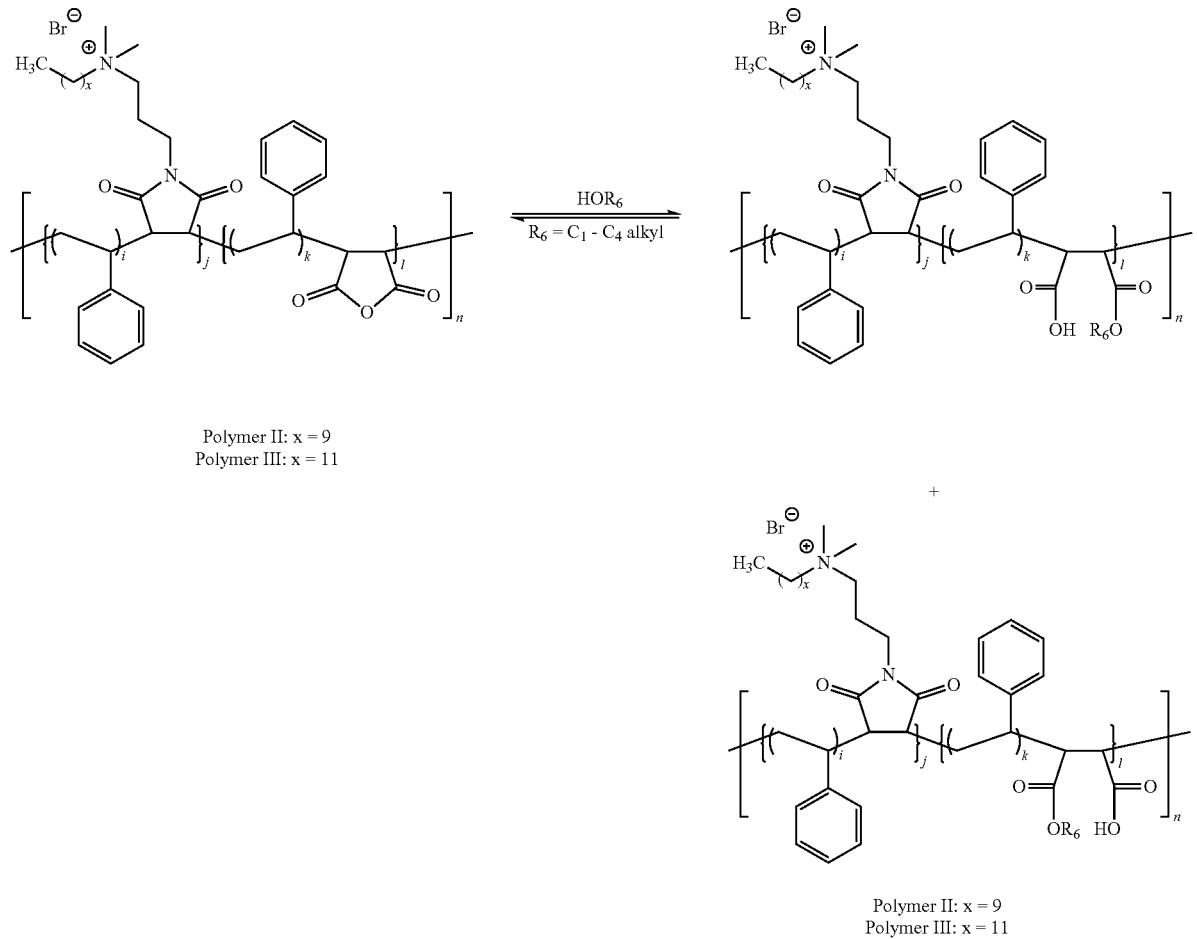

Polymer II: x = 9
Polymer III: x = 11

Coating a Wound Dressing with the Antimicrobial Coating Solution

A wound dressing comprising polyester and cellulose fibers was dipped in a selected concentration of the antimicrobial coating solution and then cured under vacuum in a vacuum-oven for 1 hour at 100° C. to 110° C. The solvent evaporates during this step and the polymer covalently bonds to the fibers of the dressing. Covalent bonding was confirmed by placing cured antimicrobial dressings in a solvent for the polymer (methanol) for 24 hours after which the textile retained its antimicrobial properties.

Antimicrobial Assays

In order to assess whether the antimicrobial wound dressing samples can directly kill microorganisms in a low nutrient environment, an assay was developed using Resorufin dye as an indicator of cell metabolism and cell viability. Resazurin (blue dye compound) is reduced to Resorufin (red/pink dye compound with fluorescent properties) by actively respiring cells.

Triplicate samples of untreated and treated (coated with the antimicrobial polymer) wound dressing were placed in black 96-well microtiter plates after which PBS (100 μL) were added to each of the wells. A mid log phase bacterial culture of *Micrococcus luteus* (*M. luteus*) was diluted to an optical density at 620 nm (OD620) of 0.20 of which 5 μL was transferred to each of the wells. The plate was incubated at 37° C. for 1 hour after which 10 μL of Resazurin (0.3 mg/mL) was added to each well. The plate was again incubated for 2 hours at 37° C. After the incubation, the fluorescence (F) was determined at an excitation wavelength of 530 nm and an emission wavelength of 590 nm. Cell viability was calculated with the equation:

$$\% \text{ cell viability} = 100 \times \frac{F_{well} - \langle F_{no\ growth} \rangle}{\langle F_{growth\ control} \rangle - \langle F_{no\ growth} \rangle}$$

Fluorescence readings were taken with a Varioskan™ Multimode reader from Thermo Scientific™ controlled by Skanlt Software 2.4.1 from Thermo Electron. Each plate was shaken for 5 seconds before readings were taken at 25° C.

The high-throughput assays were performed on both untreated and treated wound dressing samples. The treated samples were coated and cured with antimicrobial coating solutions of 2 wt %, 4 wt %, 10 wt % and 20 wt % of Polymer II. These antimicrobial coating solutions include the Polymer II, methanol and trace amounts of DMSO. 90 mol % of the maleic anhydride residues in the bulk of Polymer II (which are in an approximate 1:1 ratio with the styrene monomers) have been modified to include quaternary ammonium Br-salt moieties which include a $C_{10}$ alkyl chain.

Further experiments were conducted with wound dressing samples coated with 2 wt %, 4 wt %, 10 wt % and 20 wt % of Polymer III in which 90 mol % of the maleic anhydride residues were modified to include a quaternary ammonium Br-salt moiety and a $C_{12}$ alkyl chain. The 10% remaining maleic anhydride residues were crosslinked to the wound dressing samples to covalently bind Polymer III thereto. These experiments were conducted to compare the antimicrobial activity of Polymer III with Polymer II in respect of *M. luteus*, a gram positive bacteria. The results are shown in FIG. 1 which illustrates that Polymer II (represented as Q10 in FIG. 1) is more effective at reducing the cell viability of *M. luteus* than Polymer III (represented as Q12 in FIG. 1). In dressings treated with a 2 wt % Polymer II solution, the cell viability of *M. luteus* was reduced by approximately 65%.

Figure 2:
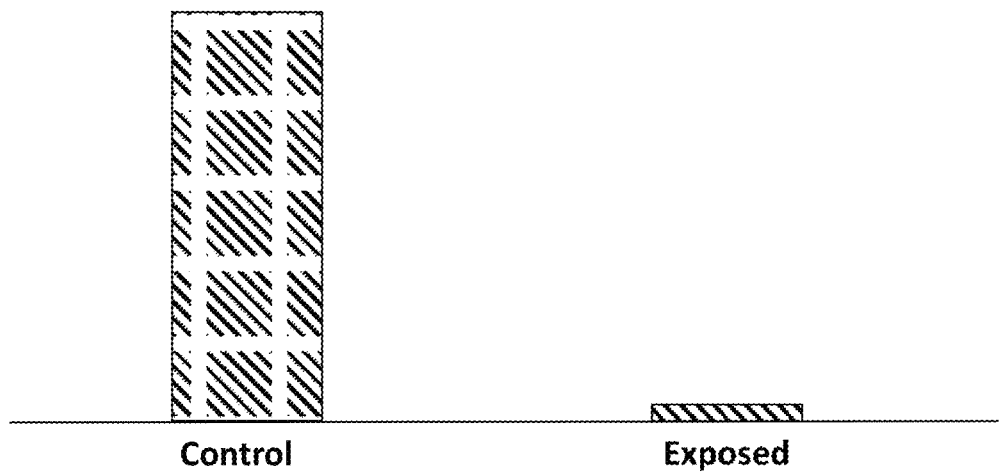
FIG. 2 is a bar graph that plots the percentage cell viability of Gram positive bacterial cultures exposed to Polymer I nanofibers for one hour against a control.
Figure 3:
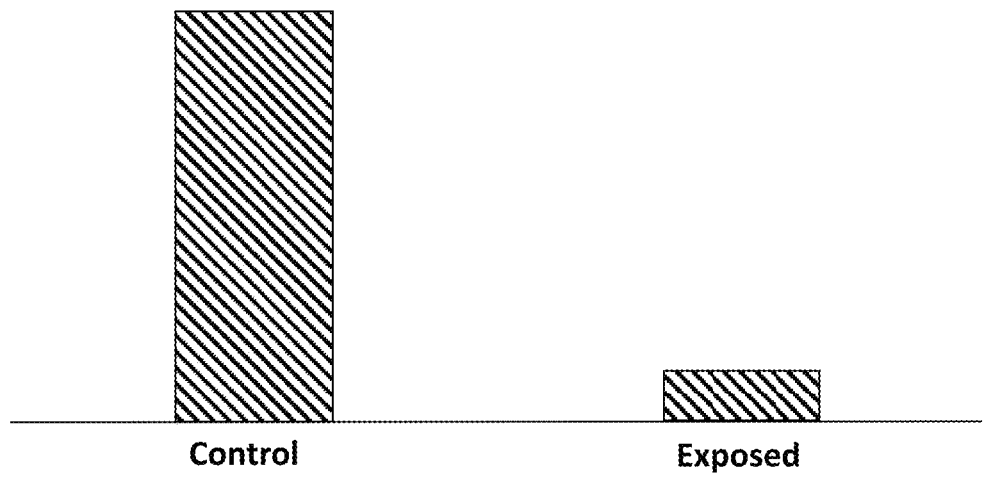
FIG. 3 is a bar graph that plots the percentage cell viability of Gram negative bacterial cultures exposed to Polymer I nanofibers for one hour against a control.

The antibacterial activity of nanofibers of Polymer I, which were produced by electrospinning, were also investigated against Gram negative and Gram positive bacterial strains. Gram positive and Gram negative bacterial cultures were respectively exposed to nanofibers of Polymer I for one hour and the results compared to a control. FIG. 2 shows the percentage of gram positive bacterial cells which are still alive after exposure to the Polymer I nanofibers for an hour compared to a control using the same bacterial cultures. FIG. 3 shows the percentage of gram negative bacterial cells which are still alive after exposure to the Polymer I nanofibers for an hour compared to a control using the same bacterial cultures.

Cytotoxicity Assay

Cytotoxic studies on the commercially available mammalian cell line, C2C12 Mouse Muscle Cells, indicate that the polymer of Formula (I) including quaternary ammonium salts which incorporate an aliphatic chain of $C_8$-$C_{15}$ ($R_2$ in the Formula (I)) are the safest and do not result in cell lysis. Tests have shown that polymers of Formula (I) including quaternary ammonium salts which incorporate an aliphatic chain of $C_1$-$C_7$ are potentially cytotoxic to the C2C12 Mouse Muscle Cells and therefore also potentially harmful to other mammalian cells.

Figure 4:
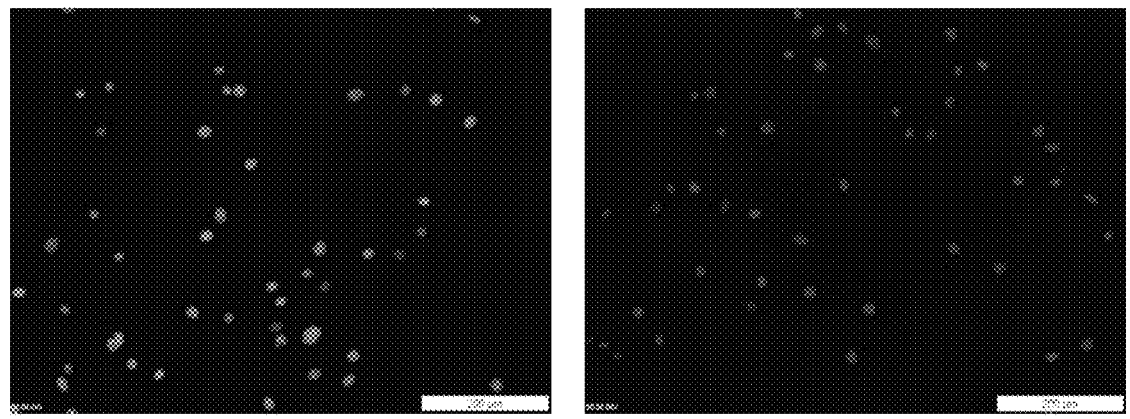
FIG. 4 shows fluorescent images of mammalian cell culture controls indicating dead cells stained red (left image) and live cells stained blue (right image)
Figure 5:
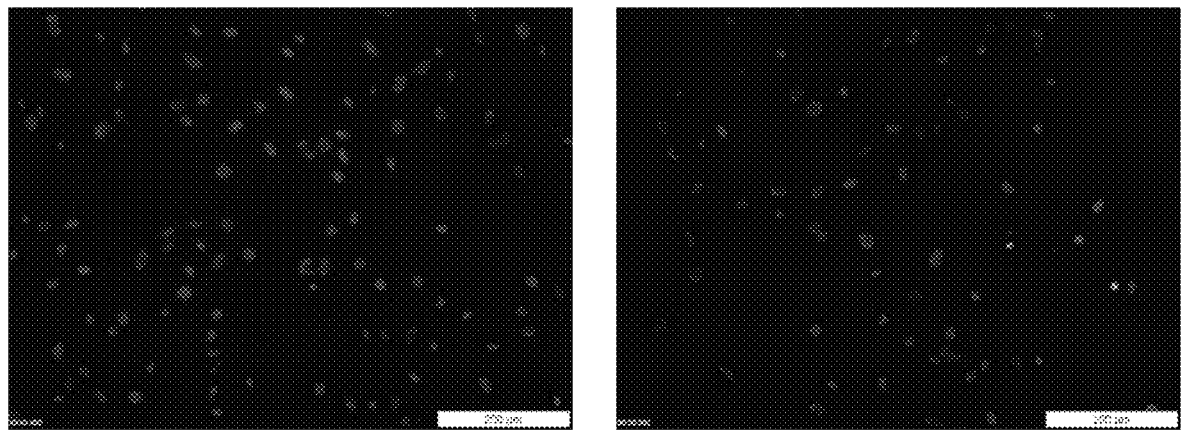
FIG. 5 shows fluorescent images of mammalian cell cultures exposed to Polymer I nanofibers for four hours.

In further experiments, C2C12 Mouse Muscle Cells in a biological growth medium consisting of Dulbecco's Modified Eagle's Medium (DMEM) growth medium, 10% Fetal Calf Serum and 1% PenStrep (combination of penicillin and streptomycin) were exposed to nanofibers of Polymer I formed by electrospinning for four hours. The cell culture was stained with two different fluorescent dyes. A red dye indicating the dead cells and a blue dye which indicates live cells. FIG. 4 shows the controls of a 100% dead cell culture stained red in the image on the left and a cell culture where all of the cells are live and stained blue in the image on the right. FIG. 5 shows the fluorescent images of cell cultures exposed to Polymer I nanofibers. Almost all of the cells are stained blue, except for two red cells visible in the lower, right-hand side region of the right-hand side image of FIG. 5. The two cells that stained red can be attributed to natural cell death and not to a toxic effect. The results therefore indicate that there was no significant cell death upon exposure of the cell cultures to the Polymer I nanofibers.

In summary, Polymer I in its nanofiber form has been shown to be non-toxic to mammalian cells (C2C12 Mouse Muscle Cells) for up to four hours while these nanofibers, exposed to Gram positive and Gram negative bacteria, kill most bacterial cells in a period of one hour. It has been shown that the Polymer II covalently linked to a wound dressing's fibers has antimicrobial activity, indicating that the antimicrobial solution containing this polymer may be used for the production of inherently antimicrobial wound dressings. Due to the manner in which the polymer is incorporated in the wound dressing, it essentially forms part of the bulk material that the wound dressing is made of. Furthermore, it has been shown that the dressing's fiber layers remain antimicrobial despite immersion of the samples in a solvent in which the polymer is soluble (methanol) for 24 hours. This indicates that, in use, under physiological conditions when the dressing is applied to a wound, the antimicrobial polymer will not leach out of the wound dressing, thereby indicating that the dressing will not lose its antimicrobial activity over time.

Advantageously, covalent non-leaching bonds are formed between the substrate and the polymeric coating. Generally, it is important to keep post-surgery and especially burn wounds free from microbial infection. The ubiquitous use of antibiotics and biocides have led to the advent of antibiotic and biocide resistant bacteria. It is preferred to keep a wound free from bacterial contamination without the use of an active compound that "poisons" the bacteria, promoting the growth of bacteria that build up resistance to the active compound over time. Coating the wound dressing with the antimicrobial polymer permanently bonded to the dressing overcomes this problem of creating active agent resistant bacteria.

The above description is by way of example only and it should be appreciated that numerous changes and modifications may be made to the antimicrobial coating solution, the method of producing the solution and the substrates coated with it without departing from the scope of the invention. For example, the antimicrobial coating solution containing a polymer of Formula (I) may have any suitable concentration that is effective at preventing or inhibiting growth of a targeted microbe on the particular substrate which will be coated with the polymer. It will be appreciated by those skilled in the art that the antimicrobial coating solution may be applied and crosslinked to any suitable substrate and that the polymer of Formula (I) may be further modified to include maleic anhydride residues functionalised with a linking group that enable the polymer to permanently bind or covalently bond to a substrate. Accordingly, it is foreseen that any type of substrate may be coated with the polymer of Formula (I) using the antimicrobial coating solution described herein. In particular the polymer of Formula (I) will be effective in covalently bonding to textiles made of cotton, wool, silk, polyester, nylon or cellulose which provide a large surface area having suitable functional groups for covalently bonding the polymer of Formula (I) onto the textile. It is foreseen that the antimicrobial coating solution may find use in the medical field, in particular in the preparation of antimicrobial wound dressings, but it may also be incorporated in personal clothing such as the insoles of shoes for example.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

We claim:

1. A solution including an antimicrobial polymer having the structure of Formula (I):

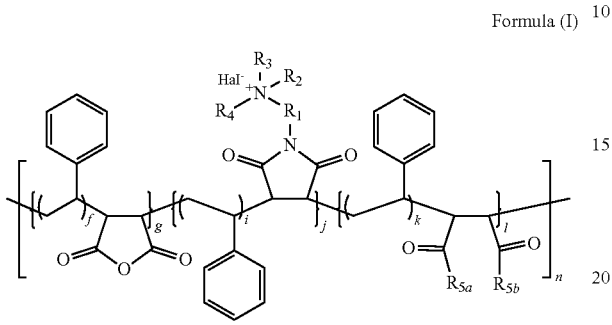

Formula (I)

wherein $R_1$ is a $C_2$-$C_7$ alkyl;
$R_2$ is a $C_8$-$C_{15}$ alkyl;
$R_{5a}$ is $O^-$ or OH and $R_{5b}$ is $OR_6$, or $R_{5b}$ is $O^-$ or OH and $R_{5a}$ is $OR_6$;
$R_3$, $R_4$ and $R_6$ are each independently a $C_1$-$C_4$ alkyl;
Hal$^-$ is a halide anion selected from the group consisting of bromide (Br$^-$), chloride (Cl$^-$) and iodide (I$^-$);
f, i, j, k and l are each independently an integer from 1 to 100;
g is an integer from 0 to 100;
the ratio of j:l is from about 1:1 to 19:1;
$0.1 < j/(g+j+l) < 1.0$; in a polar solvent and
wherein n is an integer from about 20 to about 6000.

2. The solution as claimed in claim 1 wherein the ratio of j:l is from about 4:1 to 9:1.

3. The solution as claimed in claim 1, wherein f, i and k are each independently an integer from 1 to 4.

4. The solution as claimed in claim 1, wherein $R_1$ is a $C_2$-$C_3$ alkyl.

5. The solution as claimed in claim 1, wherein $R_2$ is a $C_9$-$C_{12}$ alkyl.

6. The solution as claimed in claim 1, wherein $R_3$ and $R_4$ are methyl groups.

7. The solution as claimed in claim 1, wherein Hal$^-$ is bromide (Br$^-$).

8. A method of producing a solution including an antimicrobial polymer having the structure of Formula (I):

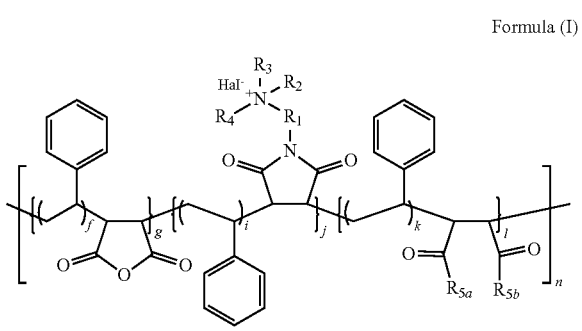

Formula (I)

wherein $R_1$ is a $C_2$-$C_7$ alkyl;
$R_2$ is a $C_8$-$C_{15}$ alkyl;
$R_{5a}$ is $O^-$ or OH and $R_{5b}$ is $OR_6$, or $R_{5b}$ is $O^-$ or OH and $R_{5a}$ is $OR_6$;
$R_3$, $R_4$ and $R_6$ are each independently a $C_1$-$C_4$ alkyl;
Hal$^-$ is a halide anion selected from the group consisting of bromide (Br$^-$), chloride (Cl$^-$) and iodide (I$^-$);
f, i, j, k and l are each independently an integer from 1 to 100;
g is an integer from 0 to 100;
the ratio of j:l is from about 1:1 to 19:1;
$0.1 < j/(g+j+l) < 1.0$; and
wherein n is an integer ranging from 20 to 6000;
the method being carried out in a polar solvent and comprising the steps of:
reacting poly(styrene-co-maleic anhydride) copolymer with N,N-dimethyl-3-amino($C_2$-$C_7$)alkyl-1-amine to form poly(styrene-co-N—(N',N'-dimethylamino-($C_2$-$C_7$)alkyl)-maleimide); and
reacting the poly(styrene-co-N—(N',N'-dimethyl-3-amino($C_2$-$C_7$)alkyl)-maleimide) with a $C_8$-$C_{15}$ alkyl bromide, chloride or iodide to produce the polymer of Formula (I).

9. The method as claimed in claim 8, wherein the reactions are carried out consecutively in the same solvent.

10. The method as claimed in claim 8, further including a step of diluting the solution containing the polymer of Formula (I) with a low boiling point solvent which has a boiling point of less than 100° C. at a pressure of 101.325 kPa.

11. The method as claimed in claim 8, wherein about 80-90 mol % of the total maleic anhydride residues in the poly(styrene-co-maleic anhydride) copolymer are converted into N—(N',N'-dimethyl-3-amino($C_2$-$C_7$)alkyl)-maleimide residues and 10%-20% of the maleic anhydride residues remain unmodified.

12. The method as claimed in claim 8, wherein the poly(styrene-co-maleic anhydride) copolymer is reacted with N,N-dimethyl-3-aminopropyl-1-amine to form poly (styrene-co-N—(N',N'-dimethylaminopropyl)-maleimide and the poly(styrene-co-N—(N',N'-dimethyl-3-aminopropyl)-maleimide) is reacted with 1-bromodecane.

13. A method of producing an antimicrobial substrate comprising the steps of:
at least partially coating a substrate or a surface thereof with the solution of claim 1; and
curing the coating to crosslink the polymer of Formula (I) to the substrate.

14. An antimicrobial substrate which includes a polymer of

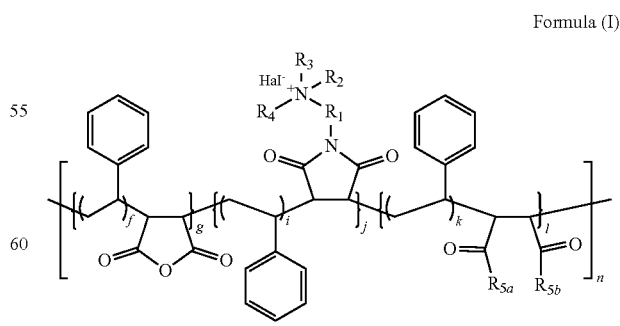

Formula (I)

Formula (I)
wherein $R_1$ is a $C_2$-$C_7$ alkyl;
$R_2$ is a $C_8$-$C_{15}$ alkyl;

$R_{5a}$ is $O^-$ or OH and $R_{5b}$ is $OR_6$, or $R_{5b}$ is $O^-$ or OH and $R_{5a}$ is $OR_6$;

$R_3$, $R_4$ and $R_6$ are each independently a $C_1$-$C_4$ alkyl;

$Hal^-$ is a halide anion selected from the group consisting of bromide ($Br^-$), chloride ($Cl^-$) and iodide ($I^-$);

f, i, j, k and l are each independently an integer from 1 to 100;

g is an integer from 0 to 100;

$0.1 < j/(g+j+l) < 1.0$; and n is an integer from about 20 to about 6000;

crosslinked to a substrate.

15. An antimicrobial substrate as claimed in claim 14 in which the substrate is a wound dressing, gauze, burn dressing, sponge, a medical or sanitary wipe, surgical gown, surgical glove, surgical scrubs, upholstery, floor mat, sheet, cover, liner, curtain or insole.

* * * * *